(12) United States Patent
Iwamoto et al.

(10) Patent No.: US 11,446,653 B2
(45) Date of Patent: Sep. 20, 2022

(54) CONTAINER SET AND SAMPLE PREPARATION METHOD USING SAME

(71) Applicant: SHIMADZU CORPORATION, Kyoto (JP)

(72) Inventors: Noriko Iwamoto, Kyoto (JP); Megumi Takanashi, Kyoto (JP); Takashi Shimada, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 892 days.

(21) Appl. No.: 16/313,669

(22) PCT Filed: Jun. 30, 2016

(86) PCT No.: PCT/JP2016/069554
§ 371 (c)(1),
(2) Date: Dec. 27, 2018

(87) PCT Pub. No.: WO2018/003104
PCT Pub. Date: Jan. 4, 2018

(65) Prior Publication Data
US 2020/0306748 A1 Oct. 1, 2020

(51) Int. Cl.
B01L 3/00 (2006.01)
B01D 35/027 (2006.01)
(Continued)

(52) U.S. Cl.
CPC .......... B01L 3/5021 (2013.01); B01D 35/027 (2013.01); B04B 3/00 (2013.01);
(Continued)

(58) Field of Classification Search
CPC .............. B01D 35/027; B01L 2200/02; B01L 2300/0681; B01L 2300/123;
(Continued)

(56) References Cited

U.S. PATENT DOCUMENTS

2010/0009832 A1  1/2010  Schaefer et al.
2015/0031040 A1  1/2015  Calanca et al.
(Continued)

FOREIGN PATENT DOCUMENTS

CN  101347384 A  1/2009
CN  201449346 U  5/2010
(Continued)

OTHER PUBLICATIONS

Noriko Iwamoto et al., "The development of the validated LCMS bioanalysis of trastuzumab in human plasma using a selective detection method for complementarity determining regions of monoclonal antibodies: nano-surface and molecular-orientation limited (nSMOL) proteolysis†", Anal. Methods, 2015, pp. 9177-9183, vol. 21.

(Continued)

Primary Examiner — Jennifer Wecker
Assistant Examiner — Kathryn Elizabeth Limbaugh
(74) Attorney, Agent, or Firm — Sughrue Mion, PLLC

(57) ABSTRACT

A container set including: a filter unit; and a closing unit that is attachable to and detachable from the filter unit. The filter unit includes: a housing having a sample introduction opening provided at one end, and a liquid discharging opening provided at the second end; and a filter fixed to the housing. The housing has a first joining part, and the closing unit has a second joining part configured to be joinable with the first joining part. The first joining part and the second joining part are configured such that the liquid discharging opening is spatially closed in a state in which the two joining parts are joined together. A space between the closing unit and the filter is made into a positive pressure relative to a pressure in the sample holding space by pushing the filter unit and the closing unit such that the distance therebetween is shortened.

4 Claims, 7 Drawing Sheets

(51) Int. Cl.
  *B04B 3/00* (2006.01)
  *G01N 1/40* (2006.01)
(52) U.S. Cl.
  CPC ......... *G01N 1/4044* (2013.01); *G01N 1/4077* (2013.01); *B01L 2200/02* (2013.01); *B01L 2300/0681* (2013.01); *B01L 2300/123* (2013.01); *B01L 2400/0409* (2013.01); *G01N 2001/4088* (2013.01)
(58) Field of Classification Search
  CPC .. B01L 2400/0409; B01L 3/5021; B04B 3/00; B04B 5/02; C12M 1/40; G01N 1/4044; G01N 1/4077; G01N 2001/4088
  See application file for complete search history.

(56) References Cited

U.S. PATENT DOCUMENTS

| | | | |
|---|---|---|---|
| 2015/0231536 | A1 | 8/2015 | Nogami et al. |
| 2016/0252522 | A1 | 9/2016 | Shimada et al. |

FOREIGN PATENT DOCUMENTS

| | | |
|---|---|---|
| JP | 62-045305 A | 2/1987 |
| JP | 2009-510398 A | 3/2009 |
| JP | 2015-509703 A | 4/2015 |
| WO | 2015/033479 A1 | 3/2015 |

OTHER PUBLICATIONS

Noriko Iwamoto et al., "Application of nano-surface and molecular-orientation limited proteolysis to LC-MS bioanalysis of cetuximab", Bioanalysis, 2016, pp. 1009-1020, vol. 8, No. 10.
International Search Report for PCT/JP2016/069554 dated Sep. 20, 2016 [PCT/ISA/210].
Written Opinion for PCT/JP2016/069554 dated Sep. 20, 2016 [PCT/ISA/237].
Communication dated Jan. 28, 2020, issued by the Intellectual Property Office of Singapore in application No. 11201811764P.
Communication dated Feb. 13, 2020, issued by the European Patent Office in application No. 16907337.6.
Office Action dated Jun. 1, 2022 issued by the European Patent Office in European Application No. 16907337.6.

CONTAINER SET AND SAMPLE PREPARATION METHOD USING SAME

CROSS REFERENCE TO RELATED APPLICATIONS

This application is a National Stage of International Application No. PCT/JP2016/069554 filed Jun. 30, 2016.

TECHNICAL FIELD

The present invention relates to a container set, and a method for preparing a sample for analysis using the container set.

BACKGROUND ART

Centrifugal filtration is excellent in solid-liquid separating performance since a liquid is transmitted through a filter so that the liquid can be separated from a solid therein. Centrifugal filtration makes use of a container set (centrifugal filtration kit) in which a filter unit into which a sample is to be charged is combined with a collecting container for collecting a liquid (filtrate) transmitted through a filter of the filter unit. The collecting container has an outer shape permitting this container to be set up to a centrifugal separator. When centrifugal separation is performed in the state that the filter unit is combined with the collecting container, a liquid component in the sample can be collected in the collecting container.

For example, in pretreatment of a sample for liquid chromatography, syringe filtration or centrifugal filtration is used to remove a solid component, such as particles or a precipitation, from the sample. After the filtration, the resultant filtrate is used, as it is, as a sample.

Centrifugal filtration is applicable also to separation (B/F separation) of a component bonded onto a solid surface (Bond) and a component not bonded to the solid surface (Free) from each other. For example, in an immunity measuring method such as ELISA (enzyme-linked immunosorbent assay), B/F separation is made to separate an antigen bonded to an antibody (Bond) from an antigen not bonded to the antibody, and other impurities (Frees). When a target sample is fixed onto a solid surface, the solid remaining on a filter after centrifugal filtration is collected. In this way, the target sample is specifically fixed onto the solid surface, and the impurities not fixed to the solid are removed as a filtrate. The solid component remaining in the filter unit, to which the target substance is fixed, is collected by an appropriate method. For example, it is advisable to add a liquid into the filter unit to suspend the solid component therein, and then collect this suspension through a pipette.

Examples of a sample preparation method using B/F separation include, besides the above-mentioned immunity measuring method, a method of site-specifically cleaving a protein by a reaction of the protein with a protease fixed onto surfaces of nano-particles to produce peptide fragments (nano-surface and molecular-orientation limited proteolysis: nSMOL method) (for example, Patent Document 1 and Non-Patent Documents 1 and 2).

FIG. 8 is a flowchart of a sample preparation and analysis according to the nSMOL method. Firstly, a porous body is prepared on which a substance to be analyzed, such as an antibody, can be selectively fixed (S10). A porous body coated with protein A, protein G, etc. can be selectively bonded to an Fc domain of an antibody. When a specimen such as plasma is added to a suspension of the porous body, the substance to be analyzed, such as the antibody, is selectively fixed into pores in the porous body (S11).

Various impurities, such as a membrane protein, adhere to the surface of the porous body. In order to dissolve and remove these impurities, the porous body is rinsed with a solution containing a surfactant (S21). By centrifugal filtration, the solid (porous body) after the rinsing is separated from the solution containing the surfactant (S22). Thereafter, the solid is rinsed with a rinsing solution such as PBS to remove the surfactant (S23). By centrifugal filtration, the solid after the rinsing is separated from the rinsing solution (S24).

Prepared are protease-fixed microparticles in which a protease such as trypsin is fixed to surfaces of nano-sized microparticles, and the microparticles are brought into contact with the above-mentioned solid in the liquid (S31). In the state that the porous body, on the surfaces of which the target substance such as the antibody is fixed, and the protease-fixed microparticles are together present in the liquid, the system is incubated, e.g., at a temperature of 35 to 60° C. for about 3 to 30 hours to conduct protease-induced proteolysis (S32). Peptide fragments which have been site-specifically cleaved with the protease are released away into the liquid.

When the particle diameter of the microparticles is larger than the pore diameter of the porous body, the protease fixed onto surfaces of the microparticles can access the vicinity of shallow parts of the pores in the porous body (the vicinity of the interface between the porous body and the liquid phase). However, the protease cannot access deep sites of the pores. Consequently, the protease specifically accesses specific moieties of the protein fixed into the pores of the porous body, so that the protein is site-specifically cleaved.

After the incubation, a liquid is collected into which peptide fragments produced by the protease-induced proteolysis are released away (S41), and then the identification and the quantitation of the protein are performed by LC-MS or some other analysis (S51).

In this method, the protein, which is to be analyzed, is site-specifically cleaved so that species of the peptides contained in the liquid sample are small. For example, when an antibody is bonded to the porous body, a limitation is imposed onto the access of the protease to an Fc domain of the antibody, which is a bonding site of the antibody to the porous body. Accordingly, an Fab domain of the antibody which contains a complementarity-determining region (CDR) is selectively cleaved with the protease. For this reason, the sample for analysis contains therein peptide fragments containing an amino acid sequence of the complementarity-determining region important for identifying the structure of the antibody at a high concentration relative to the total amount of the produced peptide fragments, so that accurate analysis becomes possible.

PRIOR ART DOCUMENTS

Patent Document

Patent Document 1: WO 2015/033479 pamphlet

Non-Patent Documents

Non-Patent Document 1: Iwamoto et al., *Anal. Methods*, 2015, 21, 9177-9183

Non-Patent Document 2: Iwamoto et al., *Bioanalysis*, 2016, 8(10), 1009-1020

SUMMARY OF THE INVENTION

Problems to be Solved by the Invention

In the above-mentioned sample preparation method, B/F separation is attained by centrifugal filtration, and subsequently protease treatment is conducted to release a substance to be analyzed into the liquid phase. The liquid is then collected as a sample for analysis. As described above, the collection of the solid after the rinsing by the B/F separation is generally attained by a pipette operation. According to the pipette operation, the solid adhering to the inside of the filter unit or chips of the pipette may remain without being collected. Consequently, the collection percentage of the sample is varied in accordance with the skill of the operator, and others. The variation causes a lowering in accuracy of quantitative analysis.

In particular, when many specimens are handled at the same time in a clinical trial and in others, works therefore easily become uneven. As operations therefore are more complicated, the effect of the accuracy-lowering is larger which is caused by the pipette operation and other operations to which the worker relates. When the number of times of a work of shifting the sample to a different container increases, the following risks are increased: the accuracy is lowered by collection loss; and further confusions of samples, and other human errors are caused. It is therefore preferred to decrease the number of times of shifting and changing containers as much as possible in the preparation of a sample for analysis in a clinical trial and others.

The filtrate is discharged by centrifugal filtration to cause the solid to remain in the filter unit (S24 in FIG. 8), and the suspension of the protease-fixed microparticles is added into the filter unit (S31 in FIG. 8). In this way, in the filter unit, protease-induced proteolysis can be attained in the filter unit without shifting the solid by any pipette operation or the like (S32 in FIG. 8). However, in the filter of the filter unit, pores are made which have a diameter of about 0.1 µm to 5 µm. Thus, the liquid storing on the filter leaks through the pores in the filter by a capillary phenomenon. When the work made is a work attained in a short period, such as an ordinary filtration, the liquid in the filter unit does not leak. However, when a reaction over a long period, such as protease-induced proteolysis, is conducted, the amount of leakage by a capillary phenomenon is increased to cause a lowering in analytical accuracy, which follows a loss of the sample.

As described above, in the case of conducting B/F separation by centrifugal filtration and subsequently performing an operation of shifting the solid from the filter unit to a different container as described above, the analytical accuracy may be lowered. In the meantime, when the state that the solid and the liquid are together present in the filter unit is continued over a long period, the liquid leaks. In the light of the problem, an object of the present invention is to provide a container and a sample preparation method about each of which a liquid does not leak easily even when a mixture of the liquid and a solid are held in a filter unit for a long period without shifting the solid from the filter unit to a different container.

Means for Solving the Problems

The container set of the present invention includes a filter unit, and a closing unit that is attachable to and detachable from the filter unit. The container set is configured such that a sample holding space of the filter unit is at a negative pressure when the filter unit and the closing unit are fitted to each other.

The filter unit has a housing, and a filter fixed into the housing. The sample holding space surrounded by the housing and the filter is configured to hold a sample (a liquid and a solid). The housing has first and second ends, and a sample introducing opening is made in the first end. The sample introducing opening is configured to allow solids and liquids to be therethrough introduced into the sample holding space. The sample introducing opening may be closable. For example, when a sample is introduced into the sample holding space, the sample introducing opening may be made into an open state. At any time expect the time of the introduction, the sample introducing opening may be closed. At the secondend of the housing, a liquid discharging opening is made for discharging the liquid (filtrate) transmitted through the filter to be sifted to the outside of the sample holding space.

The housing of the filter unit has a first joining portion joinable to the closing unit. The closing unit has a second joining portion configured to be joinable to the first joining portion of the filter unit. The first joining portion of the filter unit and the second joining portion of the closing unit have a structure in which the two are joined to each other to produce an airtight state, and the liquid discharging opening in the filter unit is spatially closed by the closing unit. The first joining portion and the second joining portion have a structure of being further pushed to each other to shorten the distance between the filter and the closing unit while the airtight state is maintained. When the filter unit and the closing unit are pushed to each other to shorten the distance between these two in the state that the first joining portion and the second joining portion are joined to each other, the space between the closing unit and the filter is turned into a positive pressure relative to the pressure in the sample holding space.

Besides the filter unit and the closing unit, the container set may include a liquid collecting container that is attachable to and detachable from the filter unit. The liquid collecting container preferably has an outer shape that can be set up to a centrifugal separator. A filtrate transmitted through the filter of the filter unit can be stored by subjecting the container set to centrifugal filtration, before the combination of the filter unit with the closing unit or after the closing unit is detached from the closing unit, in the state of combining the filter unit with the liquid collecting container.

The present invention provides a method for preparing a sample for analysis, using the above-defined container set. The sample preparation includes the following steps in turn: steps of fixing a specific substance in a specimen to a surface of a solid; removing impurities that are not fixed to the solid surface (B/F separation) by centrifugal filtration; releasing away a substance to be collected from the specific substance fixed to the solid surface to a liquid; and collecting the substance to be collected that is released away in the liquid.

The substance to be collected may be identical with the specific substance fixed to the solid surface, or may be a reaction product, decomposed product of the substance fixed to the solid surface, etc. For example, when a protein such as an antibody is fixed to the solid surface, the protein can be released away from the solid surface to the liquid in accordance with a change of the solution environment. Peptide fragments are released away into the liquid by performing protease-induced proteolysis in the state that the protein is fixed to the solid surface.

In the method of the present invention, impurities not fixed to the solid surface are removed by performing centrifugal filtration using the above-defined filter. Thereafter, a liquid such as a reaction liquid is added into the filter unit in the state that the solid is held in the sample holding space of the filter unit. In this way, the substance to be collected is released away into the liquid. In short, the centrifugal filtration and the release of the substance to be collected into the liquid are performed, using the filter unit.

After the centrifugal filtration, the filter unit is joined to the closing unit. The joining causes the substance to be collected to be released away into the liquid in the state that the liquid discharging opening in the filter unit is closed.

Effects of the Invention

The container set of the present invention has a structure in which in the state that the filter unit is combined with the closing unit, the airtightly closed space between the closing unit and the filter is at a positive pressure while the sample holding space of the filter unit is at a negative pressure. Thus, even when a sample containing a liquid is charged in the sample holding space, the liquid can be prevented from leaking through the filter.

The filter unit is usable as a centrifugal filter in the state the closing unit is separated from the filter unit. It is therefore possible to perform an operation (e.g., for reaction) of holding a sample over a long period, and rinsing or centrifugal filtration for filtrate-collection, etc., using the same filter unit. As described herein, various operations can be made in a single container, so that the number of times of conducting a work of shifting a sample to a different container can be decreased. Consequently, works of preparing the sample can be simplified, and additionally the analytical accuracy of quantitative analysis, etc. can be improved.

MODE FOR CARRYING OUT THE INVENTION

[Structure of Container Set]

The container set of the present invention includes a filter unit and a closing unit. The closing unit is attachable to and detachable from the filter unit. The container set may include a liquid collecting container that is attachable to and detachable from the filter unit.

Figure 1:
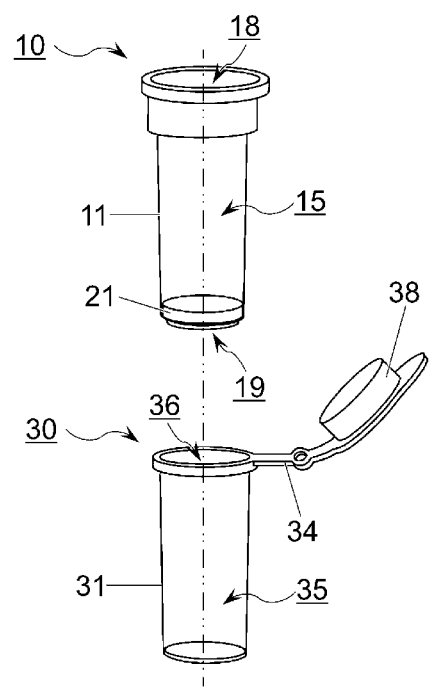
FIG. 1 is a schematic perspective view of a filter unit and a closing unit of a container set.
Figure 2A:
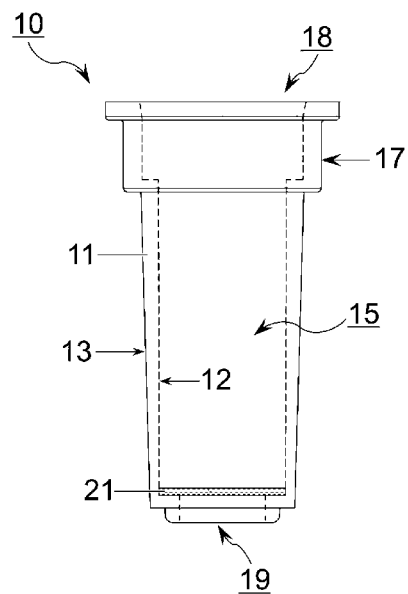
FIG. 2A is a sectional view of the filter unit.
Figure 2B:
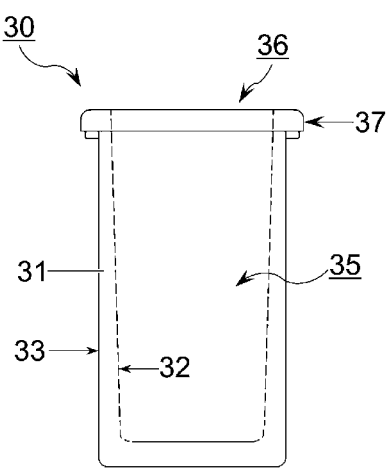
FIG. 2B is a sectional view of the closing unit.

FIG. 1 is a schematic perspective view of an embodiment of a container set including a filter unit 10 and a closing unit 30. FIG. 2A and FIG. 2B are, respectively, sectional views of the filter unit 10 and the closing unit 30.

The filter unit 10 has a structure identical or similar to a filter cup of a general spin column. A filter 21 is fixed to a housing 11 having an inner wall surface having a cylindrical shape. A sample introducing opening 18 is made at a first end of the housing 11, and a liquid discharging opening 19 is made at a second end. The filter 21 is fixed to the vicinity of a liquid discharging opening 19 in the housing 11. A space surrounded by an inner wall 12 of the housing 11, and the filter 21 constitute a sample holding space 15. The sample holding space 15 can hold solids and liquids introduced through/from the sample introducing opening 18.

The sample introducing opening 18 in the filter unit 10 may be closable at any time except the time of the introduction of a sample. For example, in the container set illustrated in FIG. 1, a lid 38 is bonded through a hinge 34 to a body portion 31 of the closing unit 30. In the state that the filter unit 10 and the closing unit 30 are combined with each other, the lid 38 can close the sample introducing opening 18. A lid for closing the sample introducing opening may be connected to the housing of the filter unit. The sample introducing opening may be closed by means of a lid independent of the filter unit and the closing unit.

The filter 21 may be a porous membrane made of polysulfone, acetylcellulose, nitrocellulose, polyvinylpyrrolidone, nylon, polyvinylidene fluoride, etc. The filter 21 has filter pores through which a liquid inside the sample holding space 15 can transmit. The pore diameter of the filter pores is set into the range of, e.g., about 0.1 to 5 μm in such a manner that any solid in the sample holding space 15 does not transmit the pores. The filter 21 is fixed to the inside of the housing 11 by using a jointing manner, such as bonding through an adhesive agent, thermal melt-bonding, or ultrasonic melt-bonding, or a fixing ring such as an O-ring. When centrifugal filtration is performed in the state that the sample holding space 15 contains a mixture of a solid and a liquid, the liquid transmitted through the filter 21 is discharged through the liquid discharging opening 19 to the outside of the filter unit.

The housing 11 of the filter unit 10 has an outer wall surface 13 in a tapered form, and is reduced in diameter toward the joined site of the housing and the closing unit 30 (toward the lower side of the figure). This tapered outer wall surface 13 becomes a joining portion when the filter unit 10 and the closing unit 30 are combined with each other.

The closing unit 30 has a body portion 31 in the form of a cylinder having a closed bottom. A joining opening 36 through which the filter unit 10 is to be inserted is made in the upper surface of the body portion 31. An inner wall surface 32 of the closing unit has a tapered shape, and is reduced in diameter from the joining opening 36 toward the bottom of the closing unit. This inner wall surface 32 has a tapered angle as the outer wall surface 13 of the housing 11 of the filter unit 10 to become a joining portion when the filter unit 10 and the closing unit 30 are combined with each other. In other words, the outer surface taper of the filter unit 10 and the inner surface taper of the closing unit 30 constitute a pair of joining portions. These two can be joined to each other in an airtight state.

When the filter unit 10 is inserted through the joining opening 36 in the closing unit 30 to a space 35 surrounded by the body portion 31, the outer wall surface 13 of the housing of the filter unit is fitted to the inner wall surface of the body of the closing unit. The closing unit 30 has a closed end at the diameter-reduced tip of the inner taper of this unit. Thus, in the state that the filter unit and the closing unit are fitted to each other, the liquid discharging opening in the closing unit is spatially closed so that an airtight state is produced.

Figure 3A:
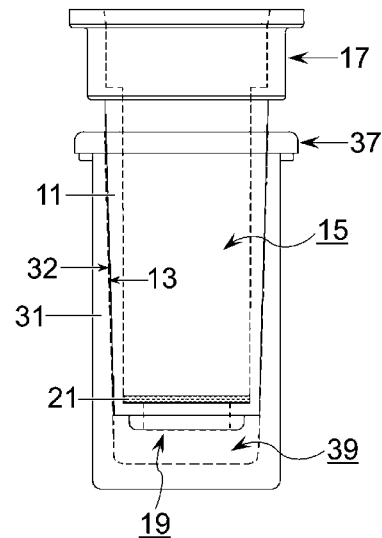
FIG. 3A is a section view of the filter unit and the closing unit in a state thereof in the middle of combining the two with each other.
Figure 3B:
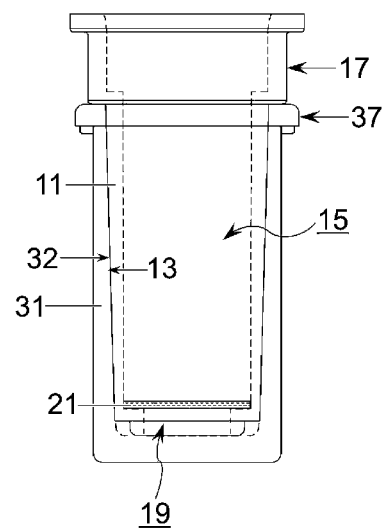
FIG. 3B is a sectional view of the filter unit and the closing unit in a state of the combination of the two with each other.

FIG. 3A is a sectional view of the filter unit 10 and the closing unit 30 in their state in the middle of combining the two with each other. FIG. 3B is a sectional view of the filter unit 10 and the closing unit 30 in a state of the combination of the two with each other. The outer wall surface 13 of the filter unit 10 and the inner wall surface 32 of the closing unit 30 have the tapered angle; therefore, when the filter unit 10 is inserted into the space 35 of the closing unit 30, the two are fitted into each other so that an airtight state is produced as illustrated in FIG. 3A.

The bottom of the body portion 31 of the closing unit is closed. Accordingly, when the outer wall surface 13 of the filter unit 10 contacts the inner wall surface 32 of the closing unit 30, the liquid discharging opening 19 in the filter unit 10 is spatially closed by the closing unit 30. In this state, the filter 21 of the filter unit 10 and the body portion 31 of the closing unit 30 turn into an airtight state, so that an airtightly closed space 39 is produced between the two.

From the state that the joining portion (outer wall surface) of the filter unit 10 is joined to the the joining portion (inner wall portion) of the closing unit 30 to produce the airtightly closed space 39, the filter unit 10 is further pushed into the closing unit 30 while the airtight state is maintained (FIG. 3B).

When the housing of the filter unit, and the closing unit are made of an elastic material such as polypropylene resin, the filter unit can be pushed into the closing unit to shorten the distance between the filter 21 of the filter unit 10, and the closing unit 30. When the filter unit is pushed into the closing unit, the housing 11 of the filter unit and the body portion 31 of the closing unit are elastically compressed to be deformed. By repulsive force thereagainst, joint state is maintained between the outer wall surface 13 of the housing 11 as a first joining portion and the inner wall surface 32 of the body portion 31 as a second joining portion. By pushing the filter unit into the closing unit, gas (air) in the airtightly closed space 39 is compressed between the filter 21 and the body portion 31 of the closing unit. Consequently, the airtightly closed space between the body portion 31 of the closing unit and the filter 21 turns into a positive pressure.

As described above, the joining portion 13 of the filter unit 10 has the outer surface tapered shape, about which the outer surface is reduced in diameter into a filter-unit-pushing direction when the filter unit 10 is pushed into the closing unit 30. The joining portion 32 of the closing unit 30 has the inner surface tapered shape, about which the inner surface is fitted to the joining portion 13 of the filter unit 10 so that an airtight state can be produced.

The tapered angle of the respective joining portions of the filter unit and the closing unit is not particularly limited. In order to push the joining portions to each other while keeping the airtightness of the joining portions, the tapered angle is preferably from about 0.1 to 10°, more preferably from about 0.2 to 5°. The tapered shape of the joining portions may be designed in accordance with any one of various standards. For example, when the tapered angle is set to 3°, joining portions in a lure rock form (lure taper), which is widely used in medical tools and tools for experiments.

When an engaging moiety 17 projected outward is made in an upper portion of the housing 11 of the filter unit, a space between the filter and the closing unit can be surely made into a positive pressure state by pushing the filter unit into the closing unit until the engaging moiety 17 contacts an outer edge portion 37 of the opening, for joining, in the closing unit. The filter unit may be pushed into the closing unit until the bottom of the closing unit contacts that of the filter unit.

When the space between the filter 21 and the closing unit 30 turns into a positive pressure, the sample holding space 15 of the filter unit 10 is at a relatively negative pressure provided that a border between the positive and negative pressures is the filter 21. When a liquid is present in the sample holding space, a capillary phenomenon causes such an effect that the liquid passes through the filter pores in the filter to leak to the outside of the sample holding space. When the space between the filter and the closing unit is at a positive pressure, an effect acts for causing gas to flow through the filter pores into the sample holding space which is at a negative pressure. Thus, even when a liquid has been held in the sample holding space, the liquid can be prevented from leaking through the filter by a capillary phenomenon.

When the filter unit 10 is used to separate a solid and a liquid from each other by centrifugal filtration, and subsequently the closing unit 30 is combined with the filter unit 10, the leakage of the liquid through the filter 21 can be restrained even in the case of adding the liquid into the sample holding space 15 of the filter unit and then keeping this state over a long period. Accordingly, even when after the centrifugal filtration a liquid is added to the filter unit to conduct a reaction, etc. without shifting any solid remaining in the filter unit into a different container, the quantitativity of the sample can be surely kept. The solid needs not be shifted into a different container through pipette operation, etc., so that operations for sample-preparation can be made simple and further the quantitativity can be prevented from being lowered by a collection loss of the solid, and others.

When the filter unit 10 and the closing unit 30 are separated from each other, the filter unit 10 is again usable as a centrifugal filter. For example, when a reaction is conducted in the state that both of a solid and a liquid are present, and subsequently centrifugal filtration is performed, the liquid after the reaction can be collected as a filtrate. After the centrifugal filtration, the solid remaining on the filter may be collected as a sample.

Figure 4:
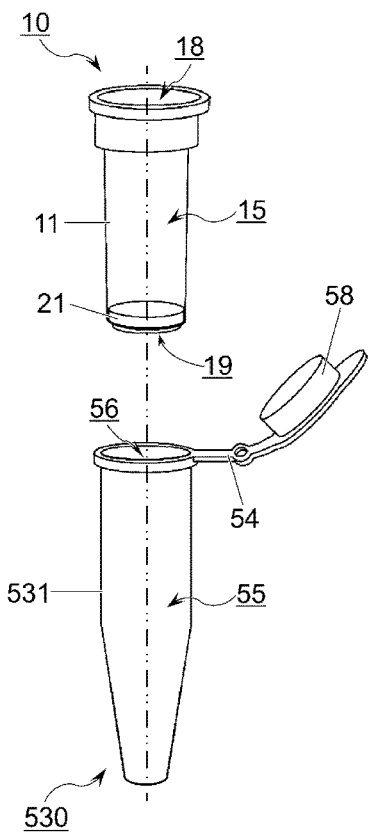
FIG. 4 is a schematic perspective view of a filter unit of a container set, and a liquid collecting container that can be combined with the filter unit.

Besides a filter unit and a closing unit, the container set may further include a liquid collecting container that is attachable to and detachable from the filter unit. FIG. 4 is a schematic perspective view of a liquid collecting container 50 that can be combined with a filter unit 10.

The liquid collecting container 50 is sufficient to be formed as follows: its body portion 51 has an outer shape which can be fitted into a centrifugal separator; and further the container can store a filtrate transmitted through a filter 21 of the filter unit 10. The outer shape that can be fitted to the centrifugal separator can be appropriately designed in accordance with the shape of a rotor of the centrifugal separator, and others. When a sample volume is small, e.g., 1 mL or less, a micro-tube or a container similar in shape thereto may be used as the liquid collecting container. The filter unit 10 and the liquid collecting container 50 do not need to have airtightness in the state that the two are combined with each other.

In the form illustrated in FIG. 4, a lid 58 is bonded through a hinge 54 to the body portion 51 of the liquid collecting container 50. In the state that the filter unit 10 and the liquid collecting container 50 are combined with each other, a sample introducing opening 18 can be closed by the lid 58.

As described above, before the filter unit 10 and the closing unit 30 are combined with each other, the filter unit 10 is used to separate a solid and a liquid from each other by centrifugal filtration. When the centrifugal filtration is performed in the state that the filter unit 10 and the liquid collecting container 50 are combined with each other, a filtrate can be collected in the liquid collecting container 50. Also after the liquid is held over a long period in the state that the filter unit 10 and the closing unit 30 are combined with each other to conduct a reaction, etc., the filter unit 10 is used to perform centrifugal filtration. Also at this time, a filtrate can be collected in the liquid collecting container by performing centrifugal filtration in the state of the combination of the filter unit 10 with the liquid collecting container 50.

In the state of the combination of the filter unit 10 with the closing unit 30, the container is smaller in height than in the state of the combination of the filter unit 10 with the liquid collecting container 50. When an adaptor is attached to the bottom of the closing unit 30 to adjust the container height, the use of a tube stand becomes easy. The closing unit may be shaped to have, below a joining portion of the unit, a space for increasing the container height.

In the embodiment illustrated in FIGS. 1 to 3, the outer wall surface 13 of the side wall of the sample holding space 15 has a tapered shape to constitute a joining portion for being joined to the closing unit. The joining portion of the filter unit may be located at a position apart from the sample holding space.

Figure 5:
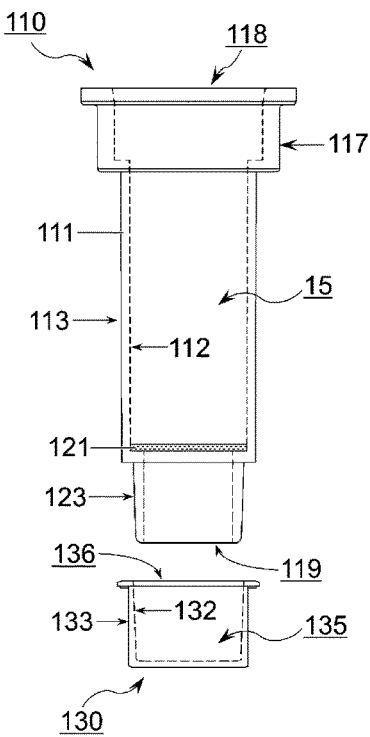
FIG. 5 is a sectional view of a filter unit and a closing unit of a container set.

For example, about a filter unit 110 illustrated in a sectional view of FIG. 5, a housing outer wall surface 123 between a filter 121 and a liquid discharging opening 119 has an outer surface tapered shape reduced in diameter toward the liquid discharging opening 119. About a closing unit 130 used in combination with this filter unit 110, its inner wall surface 132 has an inner surface tapered shape reduced in diameter from the bottom of the unit toward a joining opening 136.

In this embodiment, the outer surface taper 123 of the filter unit 110 and the inner surface taper 132 of the closing unit 130 constitute a pair of joining portions. When a housing 111 of the filter unit 110 penetrates the joining opening 136 in the closing unit 130 to be inserted into a space 135 inside the closing unit, the joining portion (outer surface taper) 123 of the filter unit 110 is fitted to the joining portion (inner surface taper) 132 of the closing unit 130 to produce an airtight state.

When the filter unit 110 is further inserted into the closing unit 130 while the airtight state by the fitting of the two is maintained, air inside the space produced between the filter 121 and the bottom of the closing unit 130 is compressed. Consequently, the airtightly closed space between the closing unit and the filter turns into a positive pressure.

The container set of the present invention is configured in such a manner that a space between its closing unit and its filter is turned into a positive pressure by inserting the closing unit into its filter unit. For example, about a filter unit 210 illustrated in a sectional view of FIG. 6, a housing inter wall surface 222 between a filter 221 and a liquid discharging opening 219 has an inter surface tapered shape reduced in diameter from a liquid discharging opening 119 toward the filter 221. About a closing unit 230 used in combination with this filter unit 210, its side surface 233 has an outer surface tapered shape reduced in diameter from the bottom of the unit toward an upper flat plane 235.

In this embodiment, the inner surface taper 222 of the filter unit 210 and the outer surface taper 233 of the closing unit 230 constitute a pair of joining portions. When the closing unit 230 is inserted into the filter unit 210 to close the liquid discharging opening 219 in this filter unit 210, the joining portion (inner surface taper) 222 of the filter unit 210 is fitted into the joining portion (outer surface taper) 233 of the closing unit 230 to produce an airtight state.

When the closing unit 230 is further inserted into the filter unit 210 while the airtight state is maintained, air inside the space produced between the filter 221 is compressed, and the upper flat plane 235 of the closing unit 230. Consequently, the airtightly closed space between the closing unit and the filter turns into a positive pressure.

The shape of the joining portion of the filter unit and the shape of the joining portion of the closing unit are not limited to tapered shapes, and may be shapes permitting the two units to be pushed to each other to shorten the distance between the filter and closing unit while the two units maintain the airtight state produced by the joint of the two joining portions.

For example, the joining portions of the filter unit and the closing unit may have screw shapes that are engaged with each other. When the closing unit is rotated relatively to the filter unit in the state that the two units are jointed to each other like the engagement of screws with each other, the distance between the filter and the closing unit is shortened so that the space between these two is compressed to produce a positive pressure state. When the joining portions have tapered screw shapes, an airtight state can be produced with a higher certainty. The joint state can be maintained even when a pressure of the space between the filter and the closing unit is increased by the engaging effect of the screws.

It is allowable to set a sealing member, such as a packing, onto the joining portion of at least one of the filter unit and the closing unit to make the filter and the closing unit into an airtight state. When one of the filter and the closing unit is pushed relatively to the other to shorten the distance between these two in the state that the joining portion of the filter and the joining portion of the closing unit have airtightness by aid of the sealing member, the airtightly closed space between the two is compressed to produce a positive pressure state.

In each of the above-mentioned embodiments, the joining portion of the filter unit and the joining portion of the closing unit are shaped to fit to each other, so that an airtight state can be produced. Another means for making the filter unit and the closing unit into an airtight state may be a method of using a film member having airtight adhesion and stretchability.

Figure 7:
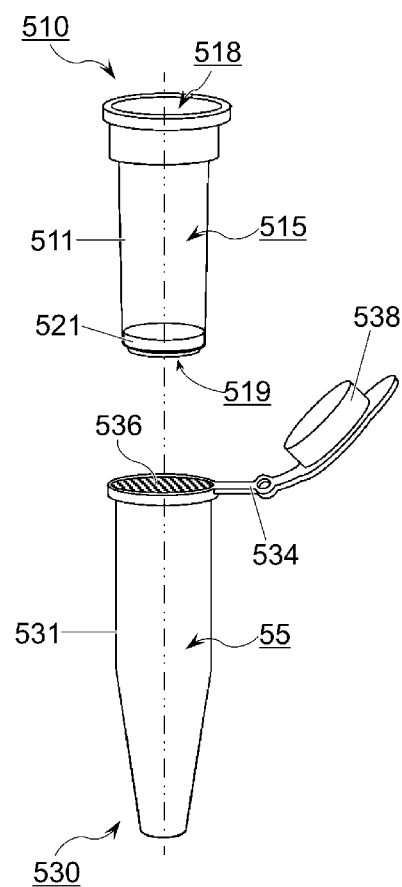
FIG. 7 is a schematic perspective view of a filter unit and a closing unit of a container set.

A container set illustrated in a perspective view of FIG. 7 includes a filter unit 510 and a closing unit 530. The filter unit 510 has the same structure as the above-mentioned individual embodiments, in which a sample introducing opening 518 is made at one of two ends of a housing 511, and a liquid discharging opening 519 is made at the second end. The outer wall surface and the inner wall surface of the housing 511 may have tapered shapes or straight pipe shapes. A filter 521 is fixed to the vicinity of the liquid discharging opening 519 in the housing 511. A space surrounded by the filter 521 and the housing 511 constitute a sample holding space 515.

The closing unit 530 has a joining opening through which a liquid discharging opening in the filter unit can pass. A film member 536 is fixed to the closing unit to close the joining opening. The film member 536 is fixed to a body portion 531 of the closing unit, for example, through an adhesive agent, or by melt-bonding or ultrasonic bonding.

The film member 536 is a film having airtight adhesion and stretchability. The film member 65 may be transparent or non-transparent. The film member 65 may be, for example, a sealing tape (tetrafluoroethylene resin unfired tape for sealing) used in joining portions of pipes; a film material used for wrapping films for food, such as ethylene vinyl acetate (EVA), polyethylene, polyvinylidene chloride or polyvinyl chloride; a "PARAFILIVI" manufactured by a company Bemis Flexible Packaging; or a "DuraSeal" manufactured by Diversified Biotech, Inc. When a liquid and a solid are caused to be present together with each other in the filter unit and are then kept for a long period, it is preferred that the film member has heat resistance and solvent resistance. It is preferred to use an ethylene based film having a softening point of 70° C. or higher, or the like.

When the liquid discharging opening 519 at one of the ends of the housing 511 of the filter unit 510 is brought into contact with the film member 536 set to a connecting opening in the closing unit, an airtight state is produced so that an airtightly closed space is produced between the filter 521 and the film member 536. In other words, in the present embodiment, the housing 511 on the outer circumference of the liquid discharging opening 519 is a joining portion of the filter unit 510, and the film member 536 corresponds to a joining portion of the closing unit 530.

When the filter unit 510 is pushed into the space 535 of the closing unit 530 in the state that the liquid discharging opening 519 in the filter unit 510 is closed by the film member 536, the film member 536 adheres closely to the housing 511 to be stretched while the airtight state of the liquid discharging opening 519 is kept. The compressing force at this time makes the space between the filter 521 and the film member 536 into a positive pressure relative to the pressure in the sample holding space 515.

In the closing unit 530 in FIG. 7, the film 536 is set to cover the opening in the micro-tube 531. However, the closing unit does not need to have a container shape. About the closing unit, the film member is sufficient to be fixed to the closing unit in such a manner that the film member covers the opening in the unit through which the filter unit can pass. The closing unit has a structure in which the film member is fixed to a ring-form shaped body. The closing unit may have a simple structure in which a film member is caused to adhere to a surface of a micro-tube stand so that the film member covers holes for standing.

Each of the embodiments of the container set has a structure in which one closing unit is combined with one filter unit. However, the container set may have a structure in which plural filter units are combined with one closing unit. For example, when a film member is bonded to a micro-tube stand in which plural micro-tubes can be arranged and held to cover the whole of the front surface of the micro-tube stand, portions of the film member that are set to individual holes in the stand function as joining portions; thus, plural filter units can be combined with each other to be held in one closing unit.

Figure 6:
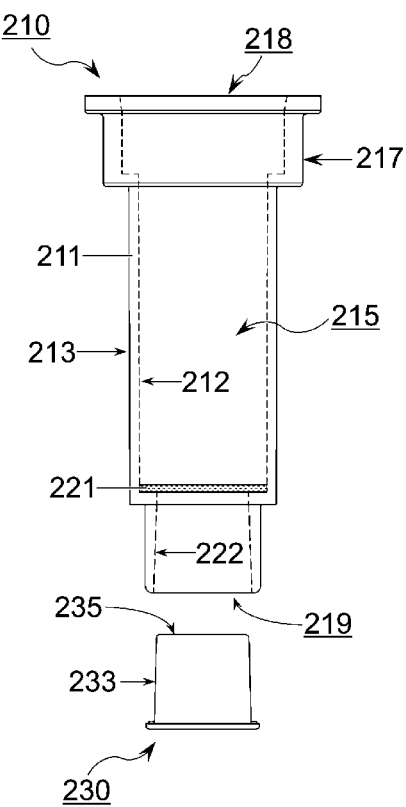
FIG. 6 is a sectional view of a filter unit and a closing unit of a container set.

The closing unit may be a plate-form member in which plural holes each having an inward tapered shape, as illustrated as the inner wall surface 32 in FIG. 2B or the inner wall surface 132 in FIG. 5, are made in a surface thereof. The closing unit may be a plate-form member in which convex portions each having an outward tapered shape, as illustrated as the side surface 233 in FIG. 6, are located on a surface thereof. As described herein, when a closing unit having plural joining portions each joinable to a filter unit is used, working efficiency can be improved in the case of treating many specimens at the same time.

[Sample Preparing Method]

The container set of the present invention is usable for sample-preparation including, for example, an operation of separating a solid and a liquid from each other by centrifugal filtration, and an operation requiring a liquid to be held in a container over a long period (e.g., for a chemical reaction). When centrifugal filtration is performed, a liquid discharging opening in the filter unit is made into an opening state and further the resultant filtrate is discharged through the liquid discharging opening to the outside of the filter unit. At this time, by setting a liquid collecting container to the filter unit, the filtrate discharged through the liquid discharging opening can be collected in the liquid collecting container.

In the sample holding space after the filtrate is discharged by the centrifugal filtration, a solid remains on the filter. In this state, the joining portion of the filter unit is joined to the joining portion of the closing unit to close the liquid discharging opening in the filter unit. By pushing the filter unit into the closing unit, the airtightly confined gas between the closing unit and the filter is compressed, so that the space turns into a positive pressure relative to the pressure in the sample holding space.

In the state that the filter unit is combined with the closing unit, a sample containing a liquid is introduced through the sample introducing opening in the filter unit into the sample holding space. The sample holding space of the filter unit is at a negative pressure relative to the pressure in the space between the closing unit and the filter, so that the liquid can be prevented from leaking through the filter by a capillary phenomenon.

It is stated herein for reference that even when only a short period, for example, a period of several minutes elapses after the liquid is introduced into the sample holding space of the filter unit, the liquid hardly leaks by a capillary phenomenon. Thus, after the liquid is introduced in the sample holding space, the filter unit can be combined with the closing unit.

After a predetermined period elapses (e.g., after the end of the reaction) in the state that the liquid is held in the sample holding space, the sample is collected. The filter unit and the closing unit are separated from each other, and then the liquid discharging opening is opened; in this way, the liquid and the solid in the sample holding space can be filtrated and separated from each other by the centrifugal filtration. At this time, by setting a liquid collecting container to the filter unit, the filtrate discharged through the liquid discharging opening can be collected in the liquid collecting container.

Figure 8:
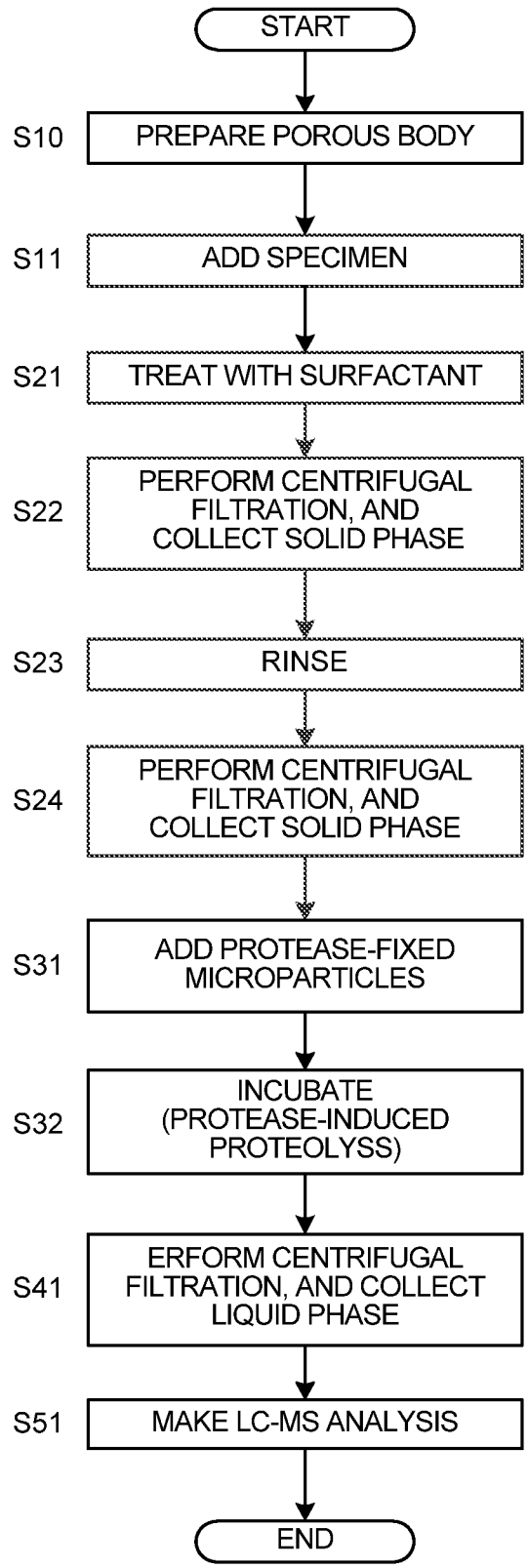
FIG. 8 is a flowchart showing an outline of a sample preparation and analysis according to the nSMOL method.

In one embodiment of the sample preparation method using the container set of the present invention, a sample for analysis is prepared from a specimen such a blood, as shown in a flowchart in FIG. 8.

Firstly, a solid is prepared which has a surface on which a specific substance in a specimen can be fixed (S10). Examples of the specimen include nucleic acids, proteins, saccharides, lipids, antibodies, receptors, antigens, ligands and other substances originating from living bodes, and cells. When the target substance is a substance originating from living bodes, the target substance may be fixed to the solid surface by molecular recognition, etc. For example, when the target substance is a nucleic acid, the use of silica-coated particles makes it possible that the nucleic acid is specifically adsorbed on surfaces of the particles. When the target substance is an antibody (such as a labelled antibody), a receptor, an antigen, a ligand, or the like, the target substance can be selectively fixed onto the solid surface through amino groups, carboxyl groups, epoxy groups, avidin, biotin, digoxigenin, protein A, or protein G.

The use of porous beads having many pores as the solid makes it possible to fix the target substance effectively onto the solid surface since the beads are large in specific surface area. According to the nSMOL method, a spatial access-limitation is set up by the use of a porous body, so that protease-induced proteolysis of the target substance can be site-specifically performed.

The specimen is added to the solid, and the two are mixed with each other so that the specific substance in the specimen is fixed onto the solid surface (S11). The mixing of the solid and the specimen may be performed in the filter unit, or in a different container.

In the state that the specific substance in the specimen is fixed to the solid surface, the solid is rinsed to remove impurities adhering onto the solid surface. When the impurities aggregate easily to adhere strongly to each other, it is preferred to use a surfactant, a chaotropic agent and the like to modify the impurities to be dissolved in the liquid (S21). After the treatment with the liquid containing the surfactant, etc., centrifugal filtration is performed to remove a filtrate containing the impurities (S22). The treatment with the surfactant, etc. and the centrifugal filtration may be repeatedly performed plural times.

After the treatment with the surfactant, rinsing with using a surfactant-free liquid is performed to wash away the surfactant adhering to the solid surface (S23). Thereafter, centrifugal filtration is performed to remove the rinsing liquid (S24). The rinsing and the centrifugal filtration can be repeatedly performed plural times.

After the impurities not fixed onto the solid surface are removed by the centrifugal filtration, the filter unit and the closing unit are combined with each other and the sample holding space in which the solid remains on the filter is made into a relatively negative pressure to prevent the leakage of the liquid by a capillary phenomenon. A liquid is added to the sample holding space and the system is kept at a predetermined temperature for a predetermined period to release away a substance to be collected from the specific substance fixed on the solid surface into the liquid.

The specific substance fixed onto the solid surface, and the substance to be collected may be the same as or different from each other. For example, when a nucleic acid is bonded to surfaces of silica-coated particles, water or a buffer liquid containing a low concentration of salt is added to weaken the interaction between silica and nucleic acid, so that the nucleic acid is released from surfaces of the silica. In this case, the specific substance fixed onto the solid surface and the substance to be collected are the same.

When the specific substance fixed onto the solid surface is caused to be related to chemical reaction in the liquid, the substance to be collected that is different from the specific substance fixed onto the solid surface is released away into the liquid. For example, when a protein is fixed onto the solid surface, peptide fragments are released away into the liquid by protease-induced proteolysis of the protein. When a protein in the specimen is fixed onto pores in a porous body, the protein can be site-specifically cleaved by bring a protease fixed onto surfaces of microparticles having a larger particle diameter than that of the pore diameter of the porous body into contact with the protein fixed into the pores since the space to which the protease can access is restricted. The micropartides, which have the surfaces onto which the protease is fixed, in the form of, e.g., suspension can be added into the sample holding space of the filter unit through the sample introducing opening (S32).

When the protein is site-specifically cleaved with a protease, it is preferred that the bonding between the solid surface and the protein is site-specific (moiety-specific). For example, protein A or protein G can be selectively bonded to an Fc domain of an antibody. Thus, the use of a porous body coated with protein A or protein G causes the Fc domain of the antibody to be fixed onto surfaces of the insides of the pores, so that the orientation of the antibody can be controlled to direct an Fab domain of the antibody into the outside of the pores. Protein A is particularly high in site-specificity in bonding with the Fc domain; thus, in order to enhance the site-specificity in protease-induced proteolysis, it is preferred to use a protein A-coated porous body.

When the orientation of an antibody is controlled in pores in a porous body as described above, a limitation is imposed onto the access of the protease to the Fc domain of an antibody, which is a bonding site thereof to the porous body. Accordingly, an Fab domain containing a complementarity-determining region (CDR) of the antibody is site-specifically cleaved with the protease. For this reason, the peptide fragments released away into the liquid contains, at a high concentration, peptide fragments including an amino acid sequence of the complementarity-determining region, which is important for the identification of the antibody.

For the protease-induced proteolysis of the protein as described above, an incubation is required usually at 35 to 60° C. for about 3 to 30 hours (S32). Even when the state that the liquid-containing sample is held in the sample holding space of the filter unit is kept for a long period, the leakage of the liquid through the filter pores in the filter can be prevented in a case where the sample holding space is at a negative pressure provided that a border between the negative and positive pressures is the filter. Accordingly, loss of the sample hardly causes so that quantitativity can be maintained.

After the substance to be collected is released away into the liquid, the filter unit and the closing unit are separated from each other. The liquid from which the substance to be collected in the filter unit is released away by the centrifugal filtration is collected, as a filtrate, into the sample collecting container (S41).

The sample yielded by the above-mentioned method is optionally subjected to dilution, desalination, purification and others, and then analyzed (S51). For example, peptide fragments prepared by the nSMOL method can be quantitatively analyzed by multiple reaction monitoring (MRM) using LC/MS/MS.

EXAMPLES

Hereinafter, a description will be made about an example of a method of using the container set of the present invention to prepare a sample by the nSMOL method on the basis of a protocol described in Non-Patent Document 2 (Iwamoto et al., *Bioanalysis,* 2016, 8(10), 1009-1020) listed above. The present invention is not limited to the example described below.

Into a 2 mL-volume microtube is fractionized and charged 25 μL of a suspension of a porous body having a surface coated with protein A (TOYOPEARL AF-rProtein A HC-650F, manufactured by Tosoh Corp.; particles diameter: 30 to 60 μm, porosity: 86%, resin concentration: 50% by weight, and IgG statically adsorbed amount: 80 g/L). Thereto are added 90 μL of a phosphoric acid buffered saline (PBS) containing 0.1% of octylβ-D-glucopyranoside, and 10 μL of a plasma sample as a specimen. This sample is gently stirred for 15 minutes. By these operations, an antibody in the plasma is fixed to the surface of the protein A-coated resin.

The suspension of the sample-fixed protein A-coated resin is shifted into the filter unit, and the resultant is subjected to centrifugal filtration at 10000 g for 1 minute. To the filter unit is added 150 µL of PBS containing 0.1% of octylβ-D-glucopyranoside, and then the resultant is subjected to centrifugal filtration at 10000 g for 1 minute. This operation is repeated 3 times to remove impurities (e.g., membrane proteins adhering to the surface of the protein A-coated resin) with the surfactant. Thereafter, 150 µL of PBS is added to the filter unit, and this system is subjected to centrifugal filtration at 10000 g for 1 minute. This operation is repeated 3 times to wash away and remove the surfactant.

The filter unit is pushed into the closing unit to combine the two units each other. The liquid discharging opening in the filter unit is closed to make this unit into an airtightly closed state. Furthermore, the filter unit is pushed into the closing unit until the engaging moiety of the filter unit contacts the closing unit. This operation compresses air between the filter unit and the closing unit to make the air into a positive pressure while the sample holding space inside the filter unit in which the protein A-coated resin is held is made into a relatively negative pressure.

Into the filter unit are added 75 µL of 25 mM tris HCl (pH: 8.0), and 10 µL of a suspension (20 mg/mL) of ferrite nanoparticles coated with polyglycidyl methacrylate and having surfaces to which trypsin is fixed (FG beads, manufactured by Tamagawa Seiki Co., Ltd.; particle diameter: about 200 nm). Under a saturated vapor pressure at 50° C., for 6 hours, gentle stirring is applied to the combination of the closing unit with the filter unit which holds a suspension of the trypsin-fixed nanoparticles and the porous resin to which the antibody in the specimen is fixed.

Protein A can be selectively bonded to the Fc domain of the antibody; thus, in the pores in the protein A-coated resin, the antibody is fixed to direct the Fab domain of the antibody outward. Since the particle diameter of the nanoparticles is larger than the pore diameter of the protein A-coated resin, trypsin fixed to the surfaces of the nanoparticles cannot access the vicinity of the bonding moieties of protein A in the pores and the Fc domain of the antibody. Accordingly, the Fab domain of the antibody is selectively cleaved with trypsin to be released away into the liquid phase.

In order to complete the proteolysis of the protein with trypsin and keep the quantitativity of this sample certainly, it is necessary to keep the liquid in the container for a long period (e.g., 6 hours as described above). In the present example, the filter unit and the closing unit are combined with each other so that the sample holding space side of the filter unit is at a negative pressure. Accordingly, even when the liquid is held in the sample holding space for a long period, the leakage of the liquid through the filter can be prevented to keep the quantitativity certainly.

To the sample kept at 50° C. for 6 hours is added 5 µL of 10% formic acid to dilute the sample liquid. Thereafter, the closing unit is separated from the filter unit, and then a new collecting container is combined with the closing unit. The resultant system is subjected to centrifugal filtration at 10000 g for 1 minute to collect the filtrate in the collecting container. This filtrate is subjected to an LC-MS analysis to identify and quantitatively analyze the antibody contained in the specimen.

In the present example, the single filter unit is used without shifting the solid into a different container in the middle of the operation, the following are performed: the rinsing of the solid to which the antibody is fixed; enzyme reaction with trypsin; and the collection of the liquid phase after the enzyme reaction. It is therefore possible to simplify the preparing working of the sample, and further prevent a collection loss caused by a variation in artificial manipulation and the like. At the time of the reaction with a protease in the filter unit as described above, the leakage of the liquid is restrained by combining the filter unit with the closing unit. It is therefore possible to prepare a sample for analysis that is high in quantitativity.

DESCRIPTION OF REFERENCE SIGNS

10 filter unit
11 housing
15 sample holding space
18 sample introducing opening
19 liquid discharging opening
21 filter
13 tapered outer wall surface (first joining portion)
30 closing unit
36 joining opening
32 tapered inner wall surface (second joining portion)

The invention claimed is:

1. A method for preparing a sample for analysis from a specimen, comprising the steps, in order, of:
   fixing a specific substance in the specimen to a solid surface;
   removing impurities that are not fixed to the solid surface by centrifugal filtration;
   releasing away a substance to be collected from the specific substance fixed to the solid surface to a liquid; and
   collecting the substance to be collected that is released away in the liquid, wherein
   the centrifugal filtration and release of the substance to be collected into the liquid are performed using the same filter unit,
   the filter unit includes: a housing having two ends in which a sample introducing opening that may be closable is made at one of the two ends and a liquid discharging opening is made at another end; and a filter fixed to the housing,
   the sample introducing opening is configured such that solids and liquids can be therethrough introduced into a sample holding space surrounded by the housing and the filter,
   the liquid discharging opening is configured such that a filtrate transmitted through the filter can be therethrough discharged,
   after the centrifugal filtration, the filter unit and a closing unit are joined to each other, so that the substance to be collected is released away into the liquid in a state that the liquid discharging opening is spatially closed,
   the housing of the filter unit has a first joining portion,
   the closing unit has a second joining portion that is configured to be joinable to the first joining portion,
   the first joining portion of the filter unit and the second joining portion of the closing unit are configured such that the two joining portions are joinable to each other to produce an airtight state to close the liquid discharging opening spatially by the closing unit, and
   the filter unit and the closing unit are further pushed to each other to shorten a distance between the filter and the closing unit while the state that the two joining portions are joined is maintained, so that a space between the closing unit and the filter is made into a positive pressure relative to a pressure in the sample holding space, and the substance to be collected is released away into the liquid in this positive pressure state.

2. The method for preparing a sample for analysis according to claim 1, wherein after the substance to be collected is released away into the liquid, the filter unit and the closing unit are separated from each other, and the liquid in which the substance to be collected is released away is collected by a centrifugal filtration.

3. The method for preparing a sample for analysis according to claim 1, wherein the specific substance fixed to the solid surface is a protein, and by a proteolysis of the protein using a protease, a peptide fragment is released away, as the substance to be collected, into the liquid.

4. The method for preparing a sample for analysis according to claim 3, wherein the solid is a porous body, and the protein in the specimen is fixed into pores in the porous body, and the protease fixed to surfaces of microparticles contacts the protein fixed into the pores in the porous body, so that the protein is site-specifically cleaved and the peptide fragment is released away into the liquid.

* * * * *